United States Patent
Bae et al.

(10) Patent No.: US 11,891,617 B1
(45) Date of Patent: Feb. 6, 2024

(54) MODIFIED COMPLEX PLATFORM OF ADENO-ASSOCIATED VIRUS WITH IMPROVED RATE OF EXPRESSION OF LOADED GENES AND REDUCED GENOTOXICITY

(71) Applicant: GENECRAFT INC., Cheongju-si (KR)

(72) Inventors: Suk Chul Bae, Cheongju-si (KR); You Soub Lee, Cheongju-si (KR); Xinzi Chi, Cheongju-si (KR); Tae Geun Park, Cheongju-si (KR); Woo-Jin Kim, Seoul (KR)

(73) Assignee: GENECRAFT INC., Cheongju-si (KR)

( * ) Notice: Subject to any disclaimer, the term of this patent is extended or adjusted under 35 U.S.C. 154(b) by 0 days.

(21) Appl. No.: 18/190,630

(22) Filed: Mar. 27, 2023

(51) Int. Cl.
  *C12N 7/01* (2006.01)
  *C12N 15/86* (2006.01)

(52) U.S. Cl.
  CPC .... *C12N 15/86* (2013.01); *C12N 2750/14143* (2013.01); *C12N 2750/14145* (2013.01)

(58) Field of Classification Search
  None
  See application file for complete search history.

(56) References Cited

U.S. PATENT DOCUMENTS 11,006,679 B2 * 5/2021 Roup ............... A41D 27/20

OTHER PUBLICATIONS

Zhou, et al. (Jul. 14, 2017) "Deletion of the B-B' and C-C' regions of inverted terminal repeats reduces rAAV productivity but increases transgene expression", Scientific Reports, 7: article 5432, 13 pages. (Year: 2017).*

Mendell, et al. (2017) "Single-Dose Gene-Replacement Therapy for Spinal Muscular Atrophy", The New England Journal of Medicine, 377(18): 1713-22 (Year: 2017).*

Asaad, et al. (2023) "AAV genome modification for efficient AAV production", Heliyon, 9: e15071, 12 pages. (Year: 2023).*

Wilmott, et al. (2019) "A User's Guide to the Inverted Terminal Repeats of Adeno-Associated Virus", Human Gene Therapy Methods, 30(6): 206-213. (Year: 2019).*

Smith, et al. (2022) "Estimating the number of diseases—the concept of rare, ultra-rare, and hyper-rare", iScience, 25: 104698, 11 pages. (Year: 2022).*

Gerasimavicius, et al. (2022) "Loss-of-function, gain-of-function and dominant-negative mutations have profoundly different effects on protein structure", Nature communications, 13: 3895, 15 pages. (Year: 2022).*

Hughes, et al. (1992) Accuracy of clinical diagnosis of idiopathic Parkinson's disease: a clinic-pathological study of 100 cases, Journal of Neurology, Neurosurgery, and Psychiatry, 55: 181-84. (Year: 1992).*

Haery, et al. (2019) "Adeno-Associated Virus Technologies and Methods for Targeted Neuronal Manipulation", Frontiers in Neuroanatomy, 13: article 93, 16 pages. (Year: 2019).*

Bolt, et al. (2021) "Development challenges associated with rAAV-based gene therapies", Journal of Toxicological Sciences, 46(2): 57-68.*

Gonçalves, M. "Adeno-associated virus: from defective virus to effective vector," *Virology Journal*, 2(43):17 pgs. (2005).

* cited by examiner

*Primary Examiner* — Robert M Kelly
(74) *Attorney, Agent, or Firm* — Crowell & Moring LLP

(57) ABSTRACT

Described herein is an adeno-associated virus (AAV) complex platform including an asymmetrically modified inverted terminal repeat (ITR). The AAV complex has advantages of increased productivity and expression efficiency of a transgene, and decreased genotoxicity, by having an asymmetric ITR in which any one of two ITRs is modified. Also, described herein is a composition comprising the adeno-associated virus complex and a method of gene therapy.

9 Claims, 14 Drawing Sheets

Specification includes a Sequence Listing.

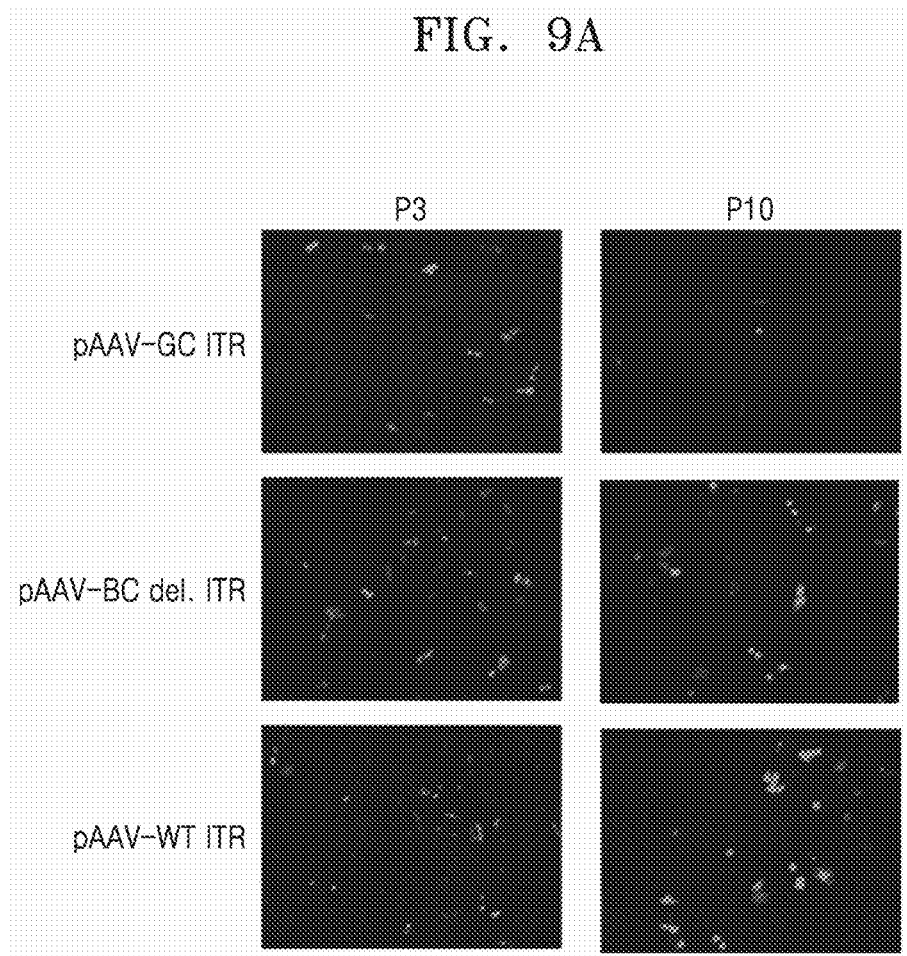

```
                        SEQUENCE LISTING

Sequence total quantity: 15
SEQ ID NO: 1            moltype = DNA  length = 58
FEATURE                 Location/Qualifiers
source                  1..58
                        mol_type = genomic DNA
                        organism = Adeno-associated virus 2
SEQUENCE: 1
aggaacccct agtgatggag ttggccactc cctctctgcg cgctcgctcg ctcactga      58

SEQ ID NO: 2            moltype = DNA  length = 56
FEATURE                 Location/Qualifiers
source                  1..56
                        mol_type = genomic DNA
                        organism = Adeno-associated virus 1
SEQUENCE: 2
ttacccctag tgatggagtt gcccactccc tctccgcgcg ctcgctcgct cggtgg        56

SEQ ID NO: 3            moltype = DNA  length = 56
FEATURE                 Location/Qualifiers
source                  1..56
                        mol_type = genomic DNA
                        organism = Adeno-associated virus 3
SEQUENCE: 3
atacctctag tgatggagtt ggccactccc tctatgcgca ctccctcgct gggtgg        56

SEQ ID NO: 4            moltype = DNA  length = 58
FEATURE                 Location/Qualifiers
source                  1..58
                        mol_type = genomic DNA
                        organism = Adeno-associated virus 4
SEQUENCE: 4
ggcaaaccta gatgatggag ttggccactc cctctatgcg cgctcgctca ctcactcg      58

SEQ ID NO: 5            moltype = DNA  length = 56
FEATURE                 Location/Qualifiers
source                  1..56
                        mol_type = genomic DNA
                        organism = Adeno-associated virus 6
SEQUENCE: 5
atacccctag tgatggagtt gcccactccc tctatgcgcg ctcgctcgct cggtgg        56

SEQ ID NO: 6            moltype = DNA  length = 58
FEATURE                 Location/Qualifiers
source                  1..58
                        mol_type = genomic DNA
                        organism = Adeno-associated virus 7
SEQUENCE: 6
cggtacccct agtgagggag ttggccactc cctctatgcg cgctcgctcg ctcggtgg      58

SEQ ID NO: 7            moltype = DNA  length = 68
FEATURE                 Location/Qualifiers
source                  1..68
                        mol_type = genomic DNA
                        organism = Adeno-associated virus 5
```

```
SEQUENCE: 7
aaaacctcct tgcttgagag tgtggcactc tcccccctgt cgcgttcgcg cgctcgctgg   60
ctcgtttg                                                            68

SEQ ID NO: 8          moltype = DNA   length = 57
FEATURE               Location/Qualifiers
source                1..57
                      mol_type = genomic DNA
                      organism = Adeno-associated virus 8
SEQUENCE: 8
ggatctcggg gttccagcgc ttgctgtttt ccttctgcag ctcccattca atttcca       57

SEQ ID NO: 9          moltype = DNA   length = 57
FEATURE               Location/Qualifiers
source                1..57
                      mol_type = genomic DNA
                      organism = Adeno-associated virus 9
SEQUENCE: 9
ggatctctgg attccagcgc ttgctgtttt ctttctgcag ctcccactcg atttcca       57

SEQ ID NO: 10         moltype = DNA   length = 23
FEATURE               Location/Qualifiers
source                1..23
                      mol_type = other DNA
                      organism = synthetic construct
SEQUENCE: 10
gtgtatcata tgccaagtac gcc                                            23

SEQ ID NO: 11         moltype = DNA   length = 24
FEATURE               Location/Qualifiers
source                1..24
                      mol_type = other DNA
                      organism = synthetic construct
SEQUENCE: 11
atcgataagc ttgatatcac cact                                           24

SEQ ID NO: 12         moltype = DNA   length = 39
FEATURE               Location/Qualifiers
source                1..39
                      mol_type = other DNA
                      organism = synthetic construct
SEQUENCE: 12
tgtatccgct catgagagct cggtcatagc tgtttcctg                           39

SEQ ID NO: 13         moltype = DNA   length = 40
FEATURE               Location/Qualifiers
source                1..40
                      mol_type = other DNA
                      organism = synthetic construct
SEQUENCE: 13
ggattttggt catgagcatg cttagaaaaa ctcatcgagc                          40

SEQ ID NO: 14         moltype = DNA   length = 25
FEATURE               Location/Qualifiers
source                1..25
                      mol_type = other DNA
                      organism = synthetic construct
misc_feature
                      note = Phosphorylation
SEQUENCE: 14
cactgactcg ctgcgctcgg tcgtt                                          25

SEQ ID NO: 15         moltype = DNA   length = 25
FEATURE               Location/Qualifiers
source                1..25
                      mol_type = other DNA
                      organism = synthetic construct
misc_feature
                      note = Phosphorylation
SEQUENCE: 15
agcgagtcag tgagcgagcg agcgc                                          25
```

MODIFIED COMPLEX PLATFORM OF ADENO-ASSOCIATED VIRUS WITH IMPROVED RATE OF EXPRESSION OF LOADED GENES AND REDUCED GENOTOXICITY

REFERENCE TO APPENDIX [CD ROM/SEQUENCE LISTING]

The instant application contains a Sequence Listing XML, which has been submitted electronically in XML format and is hereby incorporated by reference in its entirety. Said XML copy, created on Mar. 14, 2023, is named "PX069679US_SEQ Listing.xml" and is 15,342 bytes in size.

BACKGROUND

The present disclosure relates to a modified complex platform of an adeno-associated virus, and uses thereof.

An adeno-associated virus (AAV) is a single-chain DNA virus with a genome size of about 4.6 kbp, which is a helper vector-dependent human parvovirus. The genome consists of ITRs at both ends and two open reading frames (ORFs), rep and cap. The N-terminal region of the genome encodes a rep gene involved in viral replication and expression of viral genes, and the C-terminal region encodes a cap gene encoding a viral capsid protein. ITRs are involved in replication of an AAV genome and packaging of AAV particles.

On the other hand, an AAV gene delivery vehicle is safe as a delivery vehicle derived from a non-pathogenic human virus, and has a wide range of hosts without inducing a cellular immune response. In addition, an AAV gene delivery vehicle is able to deliver genes to non-dividing cells and dividing cells, and in particular, expression of a gene delivered by an AAV gene delivery vehicle is characterized by long-term persistence in vivo.

However, due to its inverted terminal repeat (ITR), the AAV has an issue of a poor DNA packaging ability because a protein-coding sequence of up to about 4.4 kb may be encapsidated. In addition, there is also an issue of a reduced rate of expression of the delivered gene, due to mutual competition between the two strands, when the gene inserted in the 3'→5' direction and the gene inserted in the 5'→3' direction are expressed in a genome of the host cell. In addition, the delivered gene has the potential to cause cancer when being inserted into the genome of the host cell.

Therefore, there is a need to develop an AAV complex as a gene delivery vehicle, with an improved DNA packaging ability, a lowered probability of insertion into the chromosome of infected cells, and improved productivity and expression efficiency, due to modification of ITR, which is a characteristic of AAVs.

SUMMARY

One embodiment described herein relates to an adeno-associated virus (AAV) complex, comprising a polynucleotide sequence encoding a transgene between a first inverted terminal repeat (ITR) and a second ITR, wherein in any one of the first ITR and the second ITR, all or part of a stem-loop structure, which is formed of rep-binding element (RBE), RBE', A, A', B, B', C, C', and D regions, is modified. The adeno-associated virus complex may further comprise an operably linked promoter, a polynucleotide sequence encoding a transgene, and a polyadenylation sequence, between the first ITR and the second ITR. The AAV may be of an AAV serotype selected from the group consisting of AAV1, AAV2, AAV3, AAV4, AAV5, AAV6, AAV7, AAV8, AAV9, AAV10, AAV11, and AAV12. In the adeno-associated virus complex, the first ITR may not be modified and the second ITR may be modified. The modification of the stem-loop structure may be at least one of an insertion, a deletion, or a substitution. In the adeno-associated virus complex, any one of the first ITR and the second ITR may be modified to not form a stem-loop structure. In the adeno-associated virus complex, in any one of the first ITR and the second ITR, all or part of a stem-loop structure, which is formed of RBE, RBE', A, A', B, B', C, C', and D regions, may be deleted. In the adeno-associated virus complex, any one of the first ITR and the second ITR may comprise a terminal resolution site (trs) sequence and an RBE sequence, and has deleted therefrom all of C, C', B', B, RBE', A' and D sequences after RBE. The promoter may be a tissue-specific promoter. In the adeno-associated virus complex, the transgene may be a therapeutic gene. In the adeno-associated virus, the transgene may be GFP, Luciferase, TP53, RPE65, TPP1, or FVIII.

Another embodiment relates to is a method of gene therapy, comprising administering an effective amount of the adeno-associated virus complex described herein to a subject in need thereof.

Yet another embodiment relates to a composition comprising the adeno-associated virus complex described herein. The composition may further comprise a pharmaceutically acceptable carrier. The composition may be for delivering a therapeutic gene for gene therapy.

BRIEF DESCRIPTION OF THE DRAWINGS

FIG. 9A shows results of taking images of GFP expression by using a fluorescence microscope at passage numbers P3 and P10.

DETAILED DESCRIPTION

Figure 1:
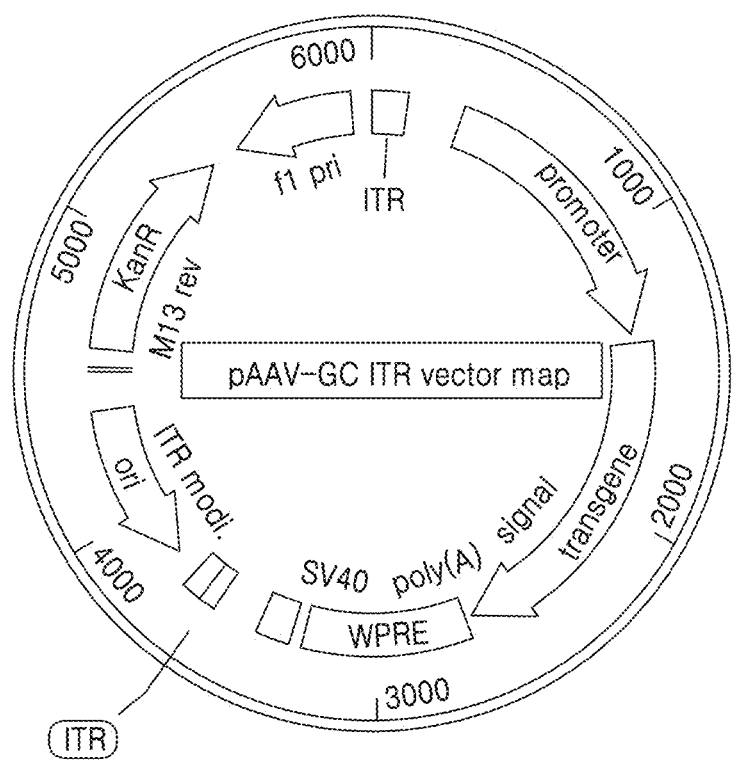
FIG. 1 shows a cleavage map of an adeno-associated virus (AAV) vector according to an example.

Reference will now be made in detail to embodiments, embodiments of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain described embodiments. As used herein, the term "and/or" includes any and all combinations of at least one of the associated listed items. Expressions such as "at least one of," when preceding a list of elements, modify the entire list of elements and do not modify the individual elements of the list.

The described embodiments, features, and advantages of certain embodiments of the disclosure will be more apparent from the following description taken in conjunction with the accompanying drawings.

One embodiment relates to an adeno-associated virus complex including a modified inverted terminal repeat.

Another embodiment relates to a cell transformed by the adeno-associated virus complex.

Yet another embodiment relates to a method of delivering a transgene, including administering an effective amount of the adeno-associated virus complex.

Yet another embodiment relates to a method of gene therapy, including administering an effective amount of the adeno-associated virus complex.

Another embodiment relates to a method of treating a disease of a subject, including administering the effective amount of the adeno-associated virus complex according to an aspect to the subject in need thereof.

Another embodiment relates to a composition including the adeno-associated virus complex.

Another embodiment relates to the use of the adeno-associated virus complex for gene therapy.

Additional embodiments will be set forth in part in the description which follows and, in part, will be apparent from the description, or may be learned by practice of the presented embodiments of the disclosure.

In one embodiment, described herein is an adeno-associated virus (AAV) complex including a modified inverted terminal repeat (ITR).

The term, "adeno-associated virus (AAV)", used herein, refers to a single-chain DNA virus with a genome size of about 4.6 kbp, which is a helper vector-dependent human parvovirus. The genome consists of ITRs at both ends and two open reading frames (ORFs), rep and cap. The N-terminal region of the genome encodes a rep gene involved in viral replication and expression of viral genes, and the C-terminal region encodes a cap gene encoding a viral capsid protein. ITRs are involved in replication of an AAV genome and packaging of AAV particles. ITR includes a rep-binding element (RBE), RBE', A, A', B, B', C, C', and D regions that form a stem-loop structure (hairpin structure).

The structure of AAV ITRs is well described, for example in Goncalves, M. A. *Virology Journal*, 2(1):43 (2005), which is incorporated herein by reference.

The ITR sequence may be based on an ITR sequence of a virus belonging to the genus Dependovirus of the family Parvoviridae.

The ITR sequence may be based on an ITR sequence of AAV. The ITR sequence of AAV is publicly known.

Examples of AAV include AAV1, AAV2, AAV3, AAV4, AAV5, AAV6, AAV7, AAV8, AAV9, AAV10, AAV11, AAV12, etc., and may also include other AAV serotypes currently known, or to be discovered later. AAV may include known AAV derivatives. AAV may include modified or artificial AAV.

Thus, the ITR sequence may be based on an ITR sequence of an AAV serotype selected from AAV1, AAV2, AAV3, AAV4, AAV5, AAV6, AAV7, AAV8, AAV9, AAV10, AAV11, and AAV12. The ITR sequence may be based on an ITR sequence of an AAV serotype selected from AAV1, AAV2, AAV3, AAV4, AAV5, AAV6, AAV7, AAV8, and AAV9. The first ITR and the second ITR may be based on ITR sequences of the same or different AAV serotypes.

Alternatively, other types of viruses belonging to the genus Dependovirus of the family Parvoviridae may be used instead of AAV.

The term "AAV complex", used herein, may be used interchangeably with "AAV vector", "AAV delivery vehicle", "recombinant AAV", and "recombinant AAV vector".

In one embodiment, the AAV complex includes a heterologous polynucleotide sequence between the first ITR and the second ITR.

The heterologous polynucleotide sequence may be operably arranged between the first ITR and the second ITR.

In one embodiment, a genome of the AAV complex includes a first ITR (5'-ITR), a polynucleotide sequence encoding a transgene, and a second ITR (3'-ITR) in a 5' to 3' direction.

In certain embodiments, the AAV complex includes a polynucleotide sequence encoding a transgene between the first ITR and the second ITR, and in any one of the first ITR and the second ITR, all or part of a stem-loop structure, which is formed of RBE, RBE', A, A', B, B', C, C', and D regions, may be modified.

In certain embodiments, the AAV complex may include an operably linked promoter, a polynucleotide sequence encoding a transgene, and a polyadenylation sequence, between a first ITR and a second ITR.

In certain embodiments, a genome of the AAV complex includes a first ITR (5'-ITR), a promoter, a polynucleotide sequence encoding a transgene, a polyadenylation sequence, and a second ITR (3'-ITR), in a 5' to 3' direction.

In certain further embodiments, the AAV complex includes an operably linked promoter, a polynucleotide sequence encoding a transgene, and a polyadenylation sequence, between the first ITR and the second ITR, and in any one of the first ITR and the second ITR, all or part of a stem-loop structure, which is formed of RBE, RBE', A, A', B, B', C, C', and D regions, may be modified.

In certain embodiments, the AAV complex may include an asymmetrically modified ITR. In an embodiment, the AAV complex may have any one of a first ITR and a second ITR modified. In another embodiment, the AAV complex may have a first ITR modified, and a second ITR not modified. In another embodiment, the AAV complex may have a first ITR not modified, and a second ITR modified. In another embodiment, the AAV complex may have 5'-ITR of a (+) strand of a transgene not modified, and 3'-ITR of the (+) strand modified. In another embodiment, the AAV complex may have 5'-ITR of the (−) strand of the transgene modified, and 3'-ITR of the (−) strand not modified. In other words, that the second ITR is modified may mean that the 3'-ITR of the (+) strand and/or the 5'-ITR of the (−) strand of the transgene is modified.

Since the AAV complex described herein may have increased productivity of the AAV complex, an increased rate of expression of the transgene, and reduced genotoxicity, by including an asymmetrically modified ITR, the AAV complex may be used as an AAV delivery vehicle platform for delivering various genes into target cells. In addition, the AAV complex described herein may be used as a delivery vehicle for expressing a transgene with high efficiency for a short time, while suppressing long-term expression of the transgene in a host cell.

Among the first ITR and the second ITR, the unmodified ITR may be a wild-type ITR. Among the first ITR and the second ITR, the unmodified ITR may be an AAV wild-type ITR.

In certain embodiments, among the first ITR and the second ITR, the unmodified ITR may be a functional derivative having substantially the same functional properties with a wild-type ITR (for example, AAV wild-type ITR).

The term "functional derivative," used herein, may mean a derivative having substantially the same functional properties. The derivative refers to a similar compound obtained by chemically changing a part of a structure of a compound. The derivative may refer to a compound in which a hydrogen atom or a specific atomic group in a compound is substituted with another atom or atomic group. A method of preparing derivatives of a compound while retaining substantially the same functional properties is known in the art.

In certain embodiments, in any one of the first ITR and the second ITR, all or part of a stem-loop structure, which is formed of RBE, RBE', A, A', B, B', C, C', and D regions, may be modified.

In an embodiment, the modification of the stem-loop structure (hairpin structure) may be selected from an insertion, a deletion, and a substitution.

In an embodiment, the modification of the stem-loop structure (hairpin structure) includes modification to include a single stem and a single loop. For example, the modified ITR may include a deletion of a B-B' arm for a C-C' arm to remain, or a deletion of the C-C' arm for the B-B' arm to remain.

In an embodiment, the modification of the stem-loop structure (hairpin structure) includes modification to include a single stem instead of two loops. For example, a modified ITR may include a deletion of a B-B' arm and a C-C' arm.

In an embodiment, the modified ITR may include a deletion of a C' region for a truncated C-loop and a B-B' arm to remain. Similarly, the modified ITR may include a deletion of a B region for a truncated B-loop and a C-C' arm to remain.

In an embodiment, the modified ITR may include a deletion of a base pair in at least one portion selected from a C portion, a C' portion, a B portion, or a B' portion, such that a single arm may be formed, for complementary base pairings occur between a C portion and a B' portion and between a C' portion and a B portion.

In an embodiment, the modified ITR may include a modification (for example, deletion, substitution, or addition) of 1, 2, 3, 4, 5, or 6 nucleotides in at least one region selected from between A' and C, between C and C', between C' and B, between B and B', and between B' and A.

In an embodiment, the modification of the stem-loop structure (hairpin structure) may include a modification of a structure of a structural element. Specifically, the modification of the structure of a structural element may include an alteration of a height of a stem and/or an alteration of a number of nucleotides in a loop. For example, the height of the stem may be about 2, 3, 4, 5, 6, 7, 8, or 9 nucleotides or more, or any range of nucleotides therein. In another example, the loop may have about 3, 4, 5, 6, 7, 8, 9, 10 nucleotides or more, or any range of nucleotides therein.

In another embodiment, by altering (for example, increasing or decreasing) a distance between two elements (as a non-limiting example, RBE and a hairpin), functional interaction with a large Rep protein may be altered. For example, the distance may be about 1, 2, 3, 4, 5, 6, 7, 8, 9, 10, 11, 12, 13, 14, 15, 16, 17, 18, 19, 20, or 21 nucleotides or more, or any range of nucleotides therein.

In an embodiment, any one of the first ITR and the second ITR may be modified to not form a stem-loop structure (hairpin structure). In another embodiment, the first ITR may be modified to not form a stem-loop structure. In another embodiment, the second ITR may be modified to not form a stem-loop structure. In another embodiment, the first ITR may not be modified, and the second ITR may be modified to not form a stem-loop structure.

The expression "modified to not form a stem-loop sequence (hairpin structure)" may mean that an ITR structure is modified to exist as an open-end or free-end without forming a stem-loop structure (hairpin structure), due to a modification of a ITR sequence.

In certain embodiments, an AAV complex is modified so that any one of the first ITR and the second ITR does not form a stem-loop structure (hairpin structure), to suppress formation of a circular dimer and circular concatemer in infected cells, and to suppress integration into the host genome, which is observed in AAV. In addition, productivity of the AAV complex and a rate of expression of the transgene may be increased by the modification.

In an embodiment, any one of the first ITR and the second ITR may be modified to a blunt end. In another embodiment, any one of the first ITR and the second ITR may be modified to a sticky end. In another embodiment, the second ITR may be modified to a blunt end or a sticky end. In another embodiment, the second ITR may be modified to a blunt end. The modification to a blunt end or a sticky end may be performed by using a known method by a person skilled in the art.

In an embodiment, in any one of the first ITR and the second ITR, all or part of a stem-loop structure, which is formed of RBE, RBE', A, A', B, B', C, C', and D regions, may be deleted. In another embodiment, in any one of the first ITR and the second ITR, part of a stem-loop structure, which is formed of RBE, RBE', A, A', B, B', C, C', and D regions, may be deleted. In another embodiment, any one of the first ITR and the second ITR may include a terminal resolution site (trs) sequence and an RBE sequence, and may have deleted therefrom all of C, C', B', B, and RBE' sequences and either A or A' region, whichever is closer to 3'-end of (+) strand of the transgene or 5'-end of (−) strand of the transgene after RBE. In another embodiment, the first ITR may not be modified, and the second ITR may include a trs sequence and an RBE sequence, and may have deleted therefrom all of C, C', B', B, and RBE' sequences and either A or A' region, whichever is closer to 3'-end of (+) strand of the transgene or 5'-end of (−) strand of the transgene after RBE.

In another embodiment, any one of the first ITR and the second ITR may include or consist of any one nucleotide sequence selected from sequences of SEQ ID NOs: 1 to 9, or a complementary sequence thereto. In another embodiment, first ITR may be not modified, and the second ITR may include or consist of any one nucleotide sequence selected from sequences of SEQ ID NOs: 1 to 9, or a complementary sequence thereto.

The sequence of SEQ ID NO: 1 may be based on a sequence of AAV2 ITR.

The sequence of SEQ ID NO: 2 may be based on a sequence of AAV1 ITR.

The sequence of SEQ ID NO: 3 may be based on a sequence of AAV3 ITR.

The sequence of SEQ ID NO: 4 may be based on a sequence of AAV4 ITR.

The sequence of SEQ ID NO: 5 may be based on a sequence of AAV6 ITR.

The sequence of SEQ ID NO: 6 may be based on a sequence of AAV7 ITR.

The sequence of SEQ ID NO: 7 may be based on a sequence of AAV5 ITR.

The sequence of SEQ ID NO: 8 may be based on a sequence of AAV8 ITR.

The sequence of SEQ ID NO: 9 may be based on a sequence of AAV9 ITR.

In certain embodiments, the sequences of SEQ ID NOs: 1 to 9 may have a portion of an AAV ITR sequence deleted. The sequences of SEQ ID NOs: 1 to 9 may include a trs sequence and a RBE sequence among AAV ITR sequences. The sequences of SEQ ID NOs: 1 to 9 may have deleted therefrom all of C, C', B', B, and RBE' regions and either A or A' region, whichever is closer to 3'-end of (+) strand of the transgene or 5'-end of (−) strand of the transgene after RBE.

In general, an RNA polymerase generates mRNA having a sequence complementary to a target gene in a promoter region. The process is called "transcription" and the transcription is proceeded in a 5' to 3' direction. Meanwhile, when a target gene is inserted into an AAV complex, the gene is inserted in the 5' to 3' direction and a 3' to 5' direction, respectively, with respect to the double helix of DNA of the AAV complex. Therefore, while transcription of the target gene is in progress, the transcription of the target gene occurs in both directions due to the double helix of DNA of the AAV complex, and thus, there is an issue that an expression efficiency of the target gene is lowered due to interference. However, an AAV complex described herein may enhance expression efficiency of a target gene by avoiding interference by the double helix structure of DNA of the AAV complex during transcription of a target gene, by a modification of the stem-loop structure, specifically, by a deletion of all or part of the stem-loop structure.

For example, in an AAV complex including an asymmetrically modified ITR, a first ITR may be not modified, and a second ITR may be modified to not form a stem-loop structure. Accordingly, 5'-ITR of the (−) strand of a transgene does not form a hairpin structure, and transcription of the transgene proceeds complementary to the corresponding strand in the 5' to 3' direction. Meanwhile, in the (+) strand of the transgene, 3'-ITR does not form a hairpin structure, and transcription of the transgene does not proceed in the corresponding strand. That is, since only the 5' to 3' direction transcription of the delivered gene proceeds, and a competitor in the 3' to 5' direction is removed, gene expression efficiency may be increased.

In an example, in an AAV vector including various transgenes, an AAV complex (pAAV-GC ITR vector) including an asymmetrically modified ITR was prepared by partially modifying a hairpin structure of a second ITR among AAV wild-type ITRs included in the vector. By comparing the prepared AAV complex with an AAV complex in which a hairpin structure is not modified (pAAV-WT ITR vector) and an AAV complex modified so that both ends of a hairpin structure are symmetrical (pAAV-BC del. ITR vector), respective productivity, a rate of expression of the transgene, and genotoxicity were confirmed. As a result, it was confirmed that the AAV complex including an asymmetrically modified ITR (pAAV-GC ITR vector), compared to the AAV complex without ITR modification (pAAV-WT ITR vector) and the AAV complex including a symmetrically modified ITR (pAAV-BC del. ITR vector), the viral productivity and rate of expression of the transgene were significantly increased, and the genotoxicity was very low.

The term "promoter," used herein, refers to a region that regulates gene transcription. The promoter may be operably linked to a coding sequence of a transgene. The promoter may be a tissue-specific promoter or an inducible promoter. The tissue-specific promoter is not limited in its type as long as the promoter induces gene expression specifically in a specific type of cell or tissue in vivo. For the tissue-specific promoter, a promoter specific for a target tissue may be appropriately selected in order that a corresponding transgene is expressed according to a type of the transgene. Non-limiting examples of the tissue-specific promoter include liver-specific thyroxin binding globulin (TBG) promoter, insulin promoter, glucagon promoter, somatostatin promoter, pancreatic polypeptide (PPY) promoter, synapsin-1 (Syn) promoter, creatine kinase (MCK) promoter, mammalian desmin (DES) promoter, α-myosin heavy chain (α-MHC) promoter, cardiac troponin T (cTnT) promoter, surfactant protein C (SPC) promoter, and the like.

The heterologous polynucleotide may encode a transgene.

The term, "transgene," used herein, refers to a gene transferred from one organism to another organism naturally, or by various genetic engineering techniques. The term "transgene" may be used interchangeably with "transferred gene" and "target gene."

The transgene is not limited to a specific type as long as it is a gene targeted to be introduced into a host cell. In certain embodiments, since an AAV complex has advantages of improved AAV productivity, an improved rate of transgene expression, and reduced genotoxicity regardless of a type of a transgene, the AAV complex may be used as an AAV delivery vehicle platform for delivering various transgenes.

In an embodiment, the transgene may be a therapeutic gene. When the transgene is a therapeutic gene, the AAV complex according to an aspect may be used as a gene therapy agent. Therefore, the AAV complex may be an AAV vector for gene therapy.

In an embodiment, the transgene may be GFP, luciferase, TP53, RPE65, TPP1, or FVIII, but is not limited thereto. When the transgene is TP53, the AAV complex for delivering the transgene may be used as a gene therapy agent for anticancer treatment. When the transgene is RPE65, the AAV complex for delivering the transgene may be used as a gene therapy agent for treating inherited retinal disease (IRD). When the transgene is TPP1 (CLN2), the AAV complex for delivering the transgene may be used as a gene therapy agent for treating Batten disease. When the transgene is FVIII, the AAV complex for delivering the transgene may be used as a gene therapy agent for treating hemophilia.

The transgene may be derived from a human or an animal.

In an embodiment, the AAV complex may further include post-transcriptional regulatory elements. The AAV complex may include a first ITR, a promoter sequence, a polynucleotide sequence encoding a transgene, post-transcriptional regulatory elements, a polyadenylation sequence, and a second ITR, in the 5' to 3' direction.

The post-transcriptional regulatory element may include a woodchuck hepatitis virus post-transcriptional regulatory element (WPRE).

In an embodiment, the AAV complex may further include a gene junction between the promoter and the polynucleotide sequence encoding a transgene.

The term "gene junction," used herein, refers to a sequence that is not defined and is located between an end of a promoter and a start of a target gene sequence. Specifically, a promoter is a site where transcription machinery is complexly bound to regulate genes, and a boundary, between the end of a known promoter sequence and the start region of a gene whose expression is to be controlled, is generally ambiguous. Thus, optimization of the junction may be needed to construct a successful promoter-gene expression relationship. A sequence of the gene junction may be appropriately selected by a person skilled in the art according to a method in the art.

The AAV complex may be engineered to encode selectable markers or reporters that provide means for selection or identification of cells that have incorporated them. Selectable markers or reporters are known in the art. Non-limiting examples of the selectable markers include genes conferring resistance to ampicillin, streptavidin, kanamycin, hygromycin, and the like. Non-limiting examples of the reporters include luciferase, green fluorescent protein (GFP), and the like.

Also, described herein is a cell transformed by an adeno-associated virus complex.

Details of the adeno-associated virus complex are as described above.

The term "transformation," used herein, means that genetic properties of an organism are changed by DNA introduced from outside. Transformation is a phenomenon in which DNA enters a cell and changes hereditary traits, when DNA, a type of nucleic acid extracted from a cell line of an organism, is injected into a living cell of another cell line. That is, "transformation" means introducing a gene into a host cell so that it may be expressed in the host cell.

A method of transforming a cell line by introducing an AAV complex described herein may be a method known in the art, for example, transient transfection by using lipofectamine, etc. microinjection, transduction, cell fusion, calcium phosphate precipitation, liposome-mediated transfection, DEAE dextran-mediated transfection, polybrene-mediated transfection, electroporation, etc., but is not limited thereto, and preferably, lipofectamine 2000 reagent may be used for transformation.

In another embodiment, described herein is a method of delivering a transgene to a subject, including administering an effective amount of an adeno-associated virus complex according to an aspect to the subject in need thereof.

Still another embodiment relates to a method of gene therapy, including administering an effective amount of an adeno-associated virus complex to a subject in need thereof.

Still another embodiment relates to a method of treating a disease of a subject, including administering an effective amount of the adeno-associated virus complex to the subject in need thereof.

In the described methods, specific details of the adeno-associated virus complex are as described above.

In the described methods, the AAV complex may be administered to a subject by itself, or the AAV complex may be formulated into a form administrable to a subject and administered to the subject. In an embodiment, the AAV complex may be administered to a subject in a form of a composition including an AAV complex. For example, the AAV complex may be formulated into a composition including the AAV complex and a pharmaceutically acceptable carrier, and administered to a subject.

The subject may be one in need of expression of a transgene delivered by the AAV complex. The subject may be one suffering from or highly likely to suffer from a disease to which gene therapy is applicable. The subject may be one suffering from or highly likely to suffer from a disease that may be treated by expression of a transgene delivered by an AAV complex. The subject may be a mammal, such as a human, a cow, a horse, a pig, a dog, sheep, a goat, or a cat.

The term "gene therapy," used herein, refers to treatment using genes to treat or prevent a disease. AAV vectors for delivering therapeutic genes into cells may be used as gene therapy agents. Diseases to which gene therapy may be easily applied include, but are not limited to, diseases caused by defects in a single gene. Non-limiting examples of diseases for which gene therapy is applicable include cancer; cardiovascular disease; genetic diseases such as inherited retinal dystrophy (IRD), Batten disease, hemophilia, cystic fibrosis, muscular dystrophy, thalassemia, and sickle cell anemia; cranial nervous system disease; infectious disease (acquired immunodeficiency syndrome, etc.); joint disease, etc.

The cancer may be a cancer in which a cancer suppressor gene is inactivated. The cancer may be, e.g., a KRAS mutated cancer. The cancer may be, e.g., a KRAS mutated solid cancer. The cancer may be, e.g., a KRAS mutated lung cancer. In certain embodiments, when activity of the cancer suppressor gene is restored, as cancer cells are removed and normal cells remain, KRAS mutated lung cancer may be treated.

The cancer suppressor gene may be, for example, sPD-1, VHL, MMAC1, DCC, p53, NF1, WT1, Rb, BRAC1, BRAC2, or RUNX3 gene.

In an embodiment, the lung cancer may be non-small cell lung cancer, or small cell lung cancer. The non-small cell lung cancer includes, for example, squamous cell carcinoma, large cell carcinoma, lung adenocarcinoma, and the like.

Accordingly, in certain embodiments, an AAV complex may prevent or treat a disease by activating a corresponding gene in a disease caused by a decrease in an activity of a specific gene, and thus, may be used for gene therapy.

The term, "prevention," used herein, refers to all actions that suppress or delay an onset of a disease by administration of the AAV complex. The term "treatment" refers to all actions that ameliorate or beneficially alter symptoms of a disease by administration of the AAV complex.

In certain embodiments, the method may further include administering a second active ingredient to the subject. The second active ingredient may be an active ingredient for preventing or treating a disease to be treated. The active ingredient may be administered concurrently, separately, or sequentially with the AAV complex.

In certain embodiments, the AAV complex may be formulated into an injectable formulation suitable for administration by any suitable route, such as intravenous, intraarterial, subcutaneous, intradermal, intraperitoneal, intramuscular, intraarticular, or intrathecal, and may be administered to a subject. The AAV complex may be administered systemically or locally, and may be administered alone or in combination with other pharmaceutically active compounds.

A preferable dosage of the AAV complex may vary depending upon the patient's condition and body weight, severity of the disease, formulation of the therapeutic agent, route and duration of administration, etc., and may be appropriately selected by those skilled in the art. In an embodiment, a dosage of the AAV complex may be about $1.0 \times 10^6$ vg/kg to about $1.0 \times 10^{16}$ vg/kg, about $1.0 \times 10^1$ vg/kg to about $1.0 \times 10^{16}$ vg/kg, about $1.0 \times 10^{10}$ vg/kg to about $1.0 \times 10^{16}$ vg/kg, about $1.0 \times 10^{10}$ vg/kg to about $1.0 \times 10^1$ vg/kg, about $1.0 \times 10^{12}$ vg/kg to about $1.0 \times 10^{14}$ vg/kg, for example, about $1.0 \times 10^{12}$ vg/kg, about $1.0 \times 10^{13}$ vg/kg, or about $1.0 \times 10^{14}$ vg/kg. In a certain embodiment, a dosage of the AAV complex may be about $1.0 \times 10^{13}$ vg/kg. The administration may be performed once a day, multiple times a day, once a week, once every 2 weeks, once every 3 weeks, or once every 4 weeks to once a year.

The term "about," used herein, is used to include a range of ±10% of a designated numerical value.

Another embodiment relates to a composition including an adeno-associated virus complex.

Still another embodiment relates to a use of the adeno-associated virus complex for gene therapy.

Details of the adeno-associated virus complex and gene therapy are as described above.

In certain embodiments, the composition may be a composition for gene therapy. The composition may be a composition for delivering a therapeutic gene for gene therapy. The composition may be a pharmaceutical composition. The composition may further include a pharmaceutically acceptable carrier. The carrier includes an excipient, a diluent, or an auxiliary agent. As the carrier, a carrier suitable for delivering the AAV complex into a living body may be used. Specifically, for the carrier, a carrier suitable for formulation into a parenteral formulation (for example, an injection formulation) may be selected. For example, for the carrier, a carrier suitable for formulation into an intravenous formulation may be selected. The carrier may be an aqueous solution, such as water or buffered saline solution and the like.

In certain embodiments, the composition may be prepared in any formulation according to a method in the art. The composition may be formulated in a form suitable for delivery of an AAV vector to a subject. The composition may be formulated in an aqueous solution, for example, in water or a buffered saline solution. Alternatively, the composition may be formulated, for example, as a parenteral formulation (for example, as an injection, for example, for bolus injection, or continuous infusion). In an embodiment, the pharmaceutical composition may be formulated as an injectable formulation suitable for administration via any suitable route, such as intravenous, intraarterial, subcutaneous, intradermal, intraperitoneal, intramuscular, intraarticular, or intrathecal. In a certain embodiment, the composition may be formulated to be administered via intravenous injection, or subcutaneous injection. In addition, the composition may be prepared as a systemic formulation, or topical formulation. The composition may be provided as ampoules, prefilled syringes, small injection containers, or a unit dosage form in multi-dose containers with added preservatives.

In certain embodiments, when the composition is used for gene therapy of a specific disease, the composition may further include a second therapeutic agent effective in preventing or treating the disease. The pharmaceutical composition may be a single composition, or separate compositions.

In certain embodiments, the composition may include an effective amount of the AAV complex. The term "effective amount" refers to an amount that is sufficient to lead to a desired preventive or therapeutic effect when administered to a subject in need thereof. The effective amount may be selected by those skilled in the art depending on the cell or the subject. The effective amount may be determined according to severity of the disease, an age, weight, health, sex, and sensitivity to a therapeutic agent of a patient, time of administration, a route of administration, an excretion rate, duration of treatment, factors including therapeutic agents used in combination with or concurrently with the composition used, and other factors well-known in the medical field. In an embodiment, the composition may include the AAV complex in a dosage of about $1.0 \times 10^6$ vg/kg to about $1.0 \times 10^{16}$ vg/kg, about $1.0 \times 10^8$ vg/kg to about $1.0 \times 10^{16}$ vg/kg, about $1.0 \times 10^{10}$ vg/kg to about $1.0 \times 10^{16}$ vg/kg, about $1.0 \times 10^{10}$ vg/kg to about $1.0 \times 10^{14}$ vg/kg, about $1.0 \times 10^{12}$ vg/kg to about $1.0 \times 10^{14}$ vg/kg, for example, about $1.0 \times 10^{12}$ vg/kg, about $1.0 \times 10^{13}$ vg/kg, or about $1.0 \times 10^{14}$ vg/kg. In a certain embodiment, the composition may include the AAV complex in a dosage of about $1.0 \times 10^{13}$ vg/kg. The administration may be performed once a day, multiple times a day, once a week, once every 2 weeks, once every 3 weeks, or once every 4 weeks to once a year.

Hereinafter, preferred examples are presented to aid understanding of the present disclosure. However, the following examples are only provided for more easier understanding the present disclosure, and the content of the present disclosure is not limited by the following examples.

EXAMPLES

Example 1. Preparation of Adeno-Associated Virus Complex Including Asymmetrically Modified ITR, for Expression of GFP Gene 1-1. Preparation of recombinant adeno-associated virus vectors in which a GFP gene is Introduced.

Recombinant adeno-associated virus (AAV) vectors in which a GFP gene is introduced were prepared. Specifically, in order to clone a chicken beta-actin promoter-GFP (CBA-GFP) gene, which is cloned into CS4-GFP vectors (Chungbuk National University Tumor Research Center), into AAV2 vectors, PCR amplification was performed by using the primers shown in Table 1 below. In this regard, the primers were prepared by synthesizing restriction enzymes NdeI and HindIII. After treating the amplified CBA-GFP DNA with restriction enzymes NdeI and HindIII, the amplified CBA-GFP DNA was cloned into a location of NdeI-HindIII in a multi-cloning site (MCS) of a wild-type adeno-associated virus (AAV)2 empty vector by using a T4 DNA ligase, to obtain AAV2-CBA-GFP plasmids. Ampicillin resistance genes were removed by using BspHI restriction enzyme sites present at both ends of the ampicillin resistance gene of the AAV2-CBA-GFP plasmids. A kanamycin resistance gene was inserted at the site from which the ampicillin resistance gene was removed. In this regard, the kanamycin resistance gene was recombined by using PCR primers in Table 1 below.

TABLE 1

| Gene | SEQ ID NO: | Direction | Sequence |
|---|---|---|---|
| CBA-GFP | 10 | Forward | 5'-gtgtatcatatgccaagtacgcc-3' |
| | 11 | Reverse | 5'-atcgataagcttgatatcaccact-3' |
| Kanamycin | 12 | Forward | 5'-TGTATCCGCTCATGAGAGCTCGGTCATAGCTGTTTCCTG-3' |
| | 13 | Reverse | 5'-GGATTTTGGTCATGAGCATGCTTAGAAAAACTCATCGAGC-3' |

1-2. Modification of ITR Structure

Site directed mutagenesis was induced, in order to modify a part of a hairpin structure of a second ITR among AAV2 wild-type inverted terminal repeats (ITRs) included in the vectors prepared in Example 1-1. Specifically, among the AAV2 wild-type ITRs included in the vector, all or at least one of C, C', B'. B, RBE', A' and D sequences after RBE of 5' direction ITR of a (−) strand of a GFP gene was deleted, by using 5'-phosphorylation primers of Table 2 below. For example, all of C, C, B', B, RBE', and A' sequences were deleted, from RBE of the 5'-direction ITR of the (−) strand of the GFP gene. Accordingly, the second ITR was modified so as not to form a hairpin structure. As a result, an AAV complex for expression of the GFP gene including an asymmetrically modified ITR, in which a first ITR was not modified and the second ITR was modified, was obtained.

The AAV vector including an asymmetrically modified ITR as in Example 1 was named pAAV-GC ITR (abbreviated as pAAV-GC).

FIG. 1 shows a cleavage map of an AAV vector according to an example.

Figure 2:
FIG. 2 shows a structure of an AAV vector according to an example.

FIG. 2 shows a structure of an AAV vector according to an example.

Figure 3A:
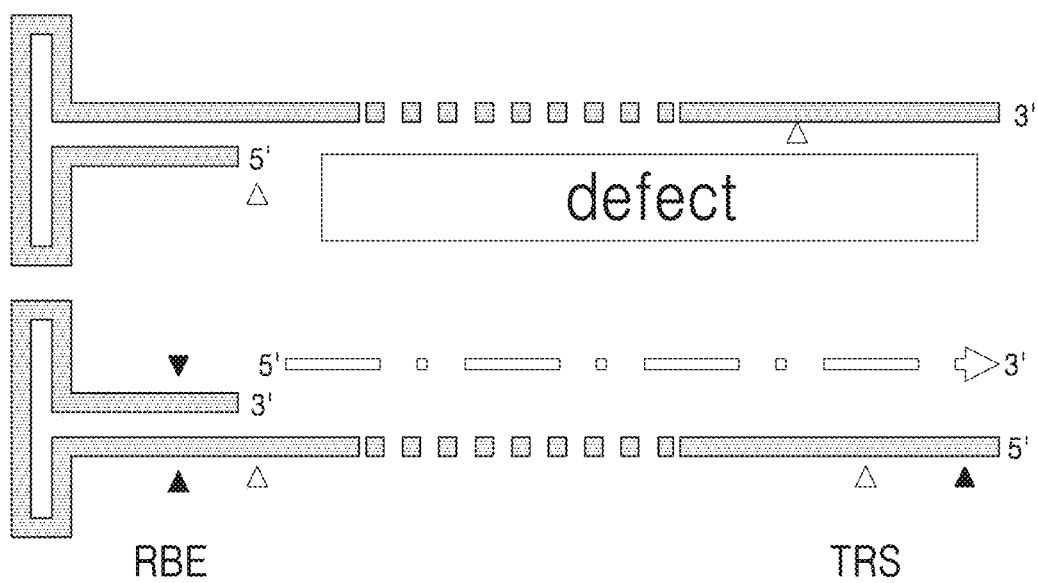
FIG. 3A is a schematic diagram of a genome of an AAV vector including an asymmetrically modified ITR of Example 1.

FIG. 3A is a schematic diagram of a genome of an AAV vector including an asymmetrically modified ITR of Example 1.

TABLE 2

| Name | SEQ ID NO: | Direction | Sequence |
|---|---|---|---|
| 5'-Phosphorylation | 14 | Forward | 5'-P-cactgactcgctgcgctcggtcgtt-3' |
| | 15 | Reverse | 5'-P-agcgagtcagtgagcgagcgagcgc-3' |

Example 2. Preparation of AAV Vector Including Asymmetrically Modified ITR, for Expression of Luciferase Gene An AAV complex, including an asymmetrically modified ITR, for expressing a luciferase gene was prepared in the same manner as in Example 1, except that the luciferase gene (2,387 bp; GenBank accession no. M15077.1) was introduced instead of the GFP gene.

Example 3. Preparation of AAV Vector Including Asymmetrically Modified ITR, for Expression of TP53 Gene An AAV complex, including an asymmetrically modified ITR, for expressing a TP53 gene was prepared in the same manner as in Example 1, except that the TP53 gene (2,512 bp; GenBank accession no. NM_000546.6) was introduced instead of the GFP gene.

Example 4. Preparation of AAV Vector Including Asymmetrically Modified ITR, for Expression of RPE65 Gene An AAV complex, including an asymmetrically modified ITR, for expressing a RPE65 gene was prepared in the same manner as in Example 1, except that the RPE65 gene (2,605 bp; GenBank accession no. NM_000329.3) was introduced instead of the GFP gene.

Example 5. Preparation of AAV Vector Including Asymmetrically Modified ITR, for Expression of TPP1 Gene An AAV complex, including an asymmetrically modified ITR, for expressing a TPP1 (CLN2) gene was prepared in the same manner as in Example 1, except that the TPP1 (CLN2) gene (1,693 bp; GenBank accession no. NM_000391.4) was introduced instead of the GFP gene.

Example 6. Preparation of AAV Vector Including Asymmetrically Modified ITR, for Expression of FVIII Gene An AAV complex, including an asymmetrically modified ITR, for expressing a FVIII gene was prepared in the same manner as in Example 1, except that the FVIII gene (673 bp; GenBank accession no. NM_000132.4) was introduced instead of the GFP gene.

COMPARATIVE EXAMPLES

Comparative Example 1. Preparation of AAV Complex Including Symmetrically Unmodified ITR, for Expression of GFP Gene An AAV complex including an unmodified symmetrical ITR was prepared in the same manner as in Example 1-1, except that an ITR hairpin structure was not modified.

The AAV vector including an unmodified symmetrical ITR as in Comparative Example 1 was named pAAV-WT ITR (abbreviated as pAAV-WT).

Figure 3B:
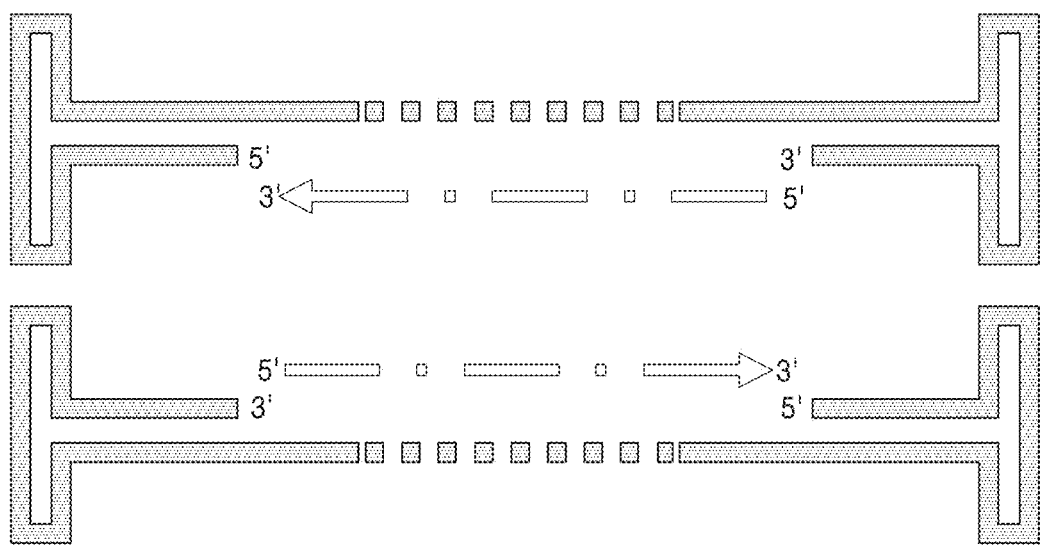
FIG. 3B is a schematic diagram of a genome of an AAV vector including an unmodified symmetrical ITR of Comparative Example 1.

FIG. 3B is a schematic diagram of a genome of an AAV vector including unmodified symmetrical ITR of Comparative Example 1.

Comparative Example 2. Preparation of AAV Complex Including Symmetrically Modified ITR, for Expression of GFP Gene An AAV complex for expressing a GFP gene, including an ITR modified in order that both ends are symmetrical to each other was prepared in the same manner as in Example 1-2, except that a C-C'-B'-RBE sequence was deleted from both ends of ITR of the AAV complex prepared in Example 1-1.

The AAV vector including a symmetrically modified ITR as in Comparative Example 2 was named pAAV-BC del. ITR (abbreviated as pAAV-BC del).

Figure 3C:
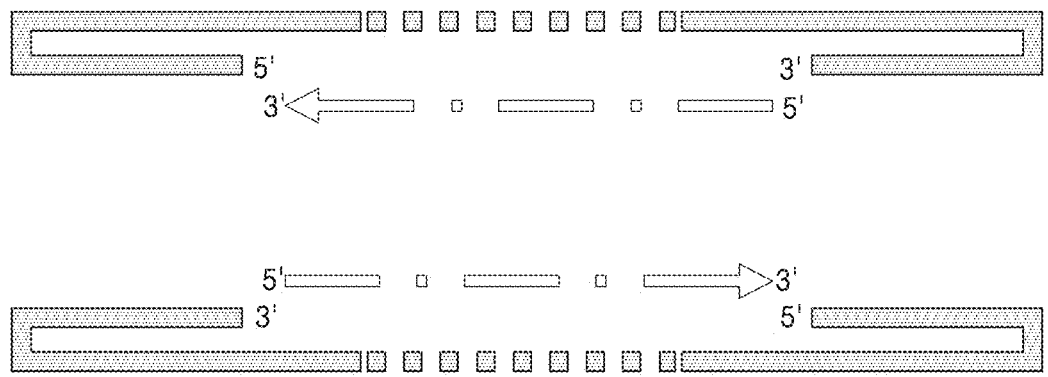
FIG. 3C is a schematic diagram of a genome of an AAV vector including a symmetrically modified ITR of Comparative Example 2.

FIG. 3C is a schematic diagram of a genome of an AAV vector including a symmetrically modified ITR of Comparative Example 2.

Comparative Example 3. Preparation of AAV Complex Including Unmodified Symmetrical ITR, for Expression of Luciferase Gene An AAV complex for expressing a luciferase gene, including an unmodified symmetrical ITR was prepared in the same manner as in Comparative Example 1, except that a luciferase gene was introduced instead of a GFP gene.

Comparative Example 4. Preparation of AAV Complex Including Symmetrically Modified ITR, for Expression of Luciferase Gene An AAV complex for expressing a luciferase gene, including a symmetrically modified ITR was prepared in the same manner as in Comparative Example 2, except that a luciferase gene was introduced instead of a GFP gene.

Comparative Example 5. Preparation of AAV Complex Including Unmodified Symmetrical ITR, for Expression of TP53 Gene An AAV complex for expressing a TP53 gene, including an unmodified symmetrical ITR was prepared in the same manner as in Comparative Example 1, except that a TP53 gene was introduced instead of a GFP gene.

Comparative Example 6. Preparation of AAV Complex Including Symmetrically Modified ITR, for Expression of TP53 Gene An AAV complex for expressing a TP53 gene, the AAV complex including a symmetrically modified ITR was prepared in the same manner as in Comparative Example 2, except that a TP53 gene was introduced instead of a GFP gene.

Comparative Example 7. Preparation of AAV Complex Including Unmodified Symmetrical ITR, for Expression of RPE65 Gene An AAV complex for expressing a RPE65 gene, the AAV complex including an unmodified symmetrical ITR was prepared in the same manner as in Comparative Example 1, except that a RPE65 gene was introduced instead of a GFP gene.

Comparative Example 8. Preparation of AAV Complex Including Symmetrically Modified ITR, for Expression of RPE65 Gene An AAV complex for expressing a RPE65 gene, the AAV complex including a symmetrically modified ITR was prepared in the same manner as in Comparative Example 2, except that a RPE65 gene was introduced instead of a GFP gene.

Comparative Example 9. Preparation of AAV Complex Including Unmodified Symmetrical ITR, for Expression of TPP1 Gene An AAV complex for expressing a TPP1 gene, the AAV complex including an unmodified symmetrical ITR was prepared in the same manner as in Comparative Example 1, except that a TPP1 gene was introduced instead of a GFP gene.

Comparative Example 10. Preparation of AAV Complex Including Symmetrically Modified ITR, for Expression of TPP1 Gene An AAV complex for expressing a TPP1 gene, the AAV complex including a symmetrically modified ITR was prepared in the same manner as in Comparative Example 2, except that a TPP1 gene was introduced instead of a GFP gene.

Comparative Example 11. Preparation of AAV Complex Including Unmodified Symmetrical ITR, for Expression of FVIII Gene An AAV complex for expressing a FVIII gene, the AAV complex including an unmodified symmetrical ITR was prepared in the same manner as in Comparative Example 1, except that a FVIII gene was introduced instead of a GFP gene.

Comparative Example 12. Preparation of AAV Complex Including Symmetrically Modified ITR, for Expression of FVIII Gene An AAV complex for expressing a FVIII gene, the AAV complex including a symmetrically modified ITR was prepared in the same manner as in Comparative Example 2, except that a FVIII gene was introduced instead of a GFP gene.

EXPERIMENTAL EXAMPLES

Experimental Example 1. Confirmation of Productivity of AAV Complex

Productivity of a recombinant AAV complex according to an embodiment was confirmed.

Specifically, the AAV complexes prepared in Examples 1 to 6 and Comparative Examples 1 to 12 were transfected into 293T cells, which are human embryonic kidney (HEK) cells. In this regard, a molar ratio of the HEK293 cell line: REP/CAP plasmid (Agilent): AAV complex was set to 1:1:1, and a AAV production method commonly used in the art was followed. AAV produced from HEK293 lysate was obtained by ultracentrifugation, and then amounts of viral proteins (VPs) and viral genomes were quantified by Western blot (WB) and qPCR, respectively. #1, #2, and #3 of qPCR are biological replicates.

Figure 4:
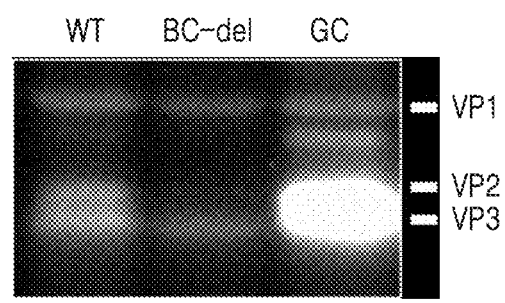
FIG. 4 is Western blot results of confirming productivity of AAVs of Example 1 (GC), Comparative Example 1 (WT) and Comparative Example 2 (BC-del) for GFP gene expression.

FIG. 4 is Western blot results of confirming productivity of AAV of Example 1 (GC), Comparative Example 1 (WT) and Comparative Example 2 (BC-del) for GFP gene expression.

Figure 5:
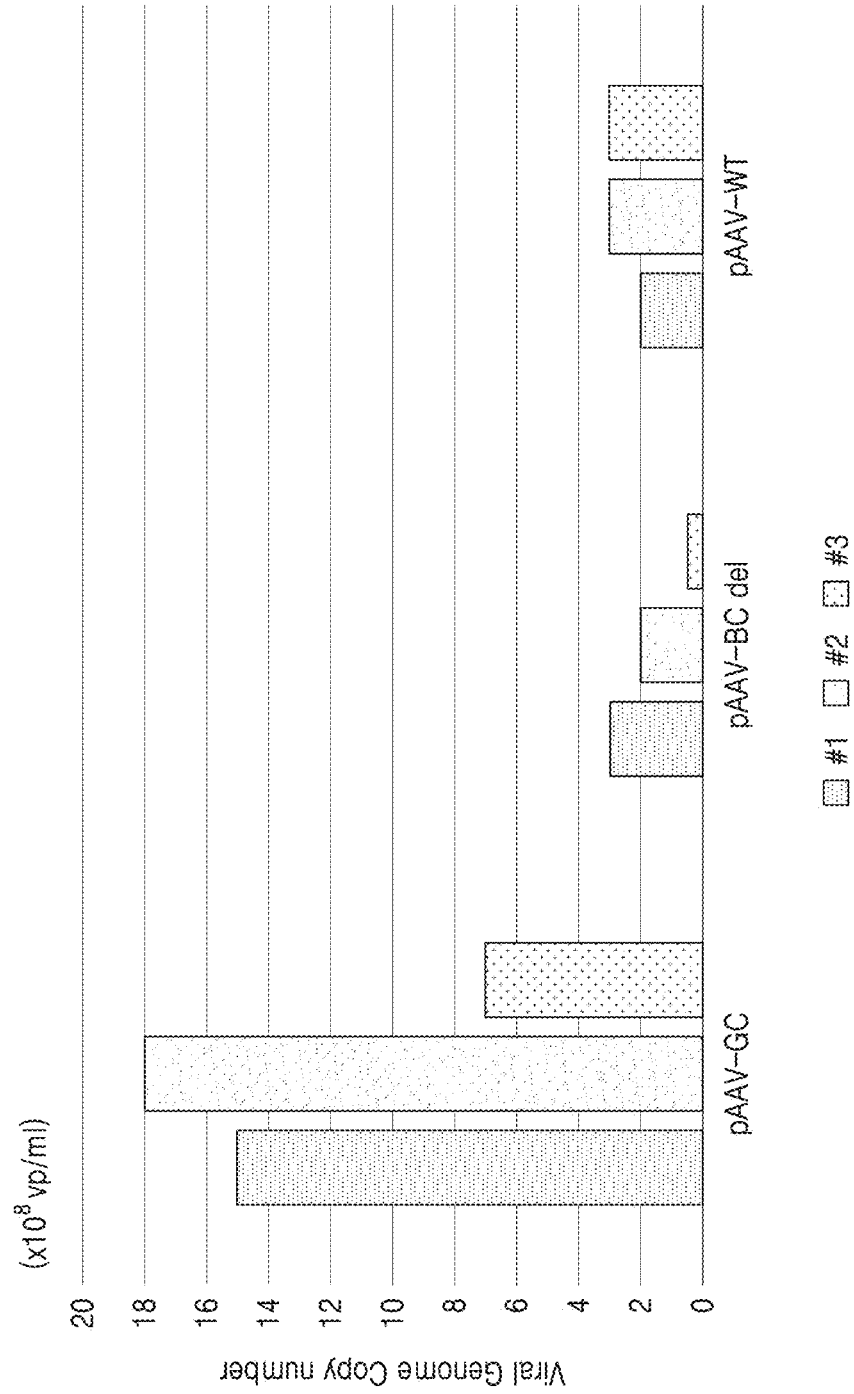
FIG. 5 is results of qPCR virus genome quantification confirming productivity of AAVs of Example 1 (pAAV-GC), Comparative Example 1 (pAAV-WT), and Comparative Example 2 (pAAV-BC del) for GFP gene expression.

FIG. 5 is results of qPCR virus genome quantification confirming productivity of AAV of Example 1 (pAAV-GC), Comparative Example 1 (pAAV-WT), and Comparative Example 2 (pAAV-BC del) for GFP gene expression.

Figure 6:
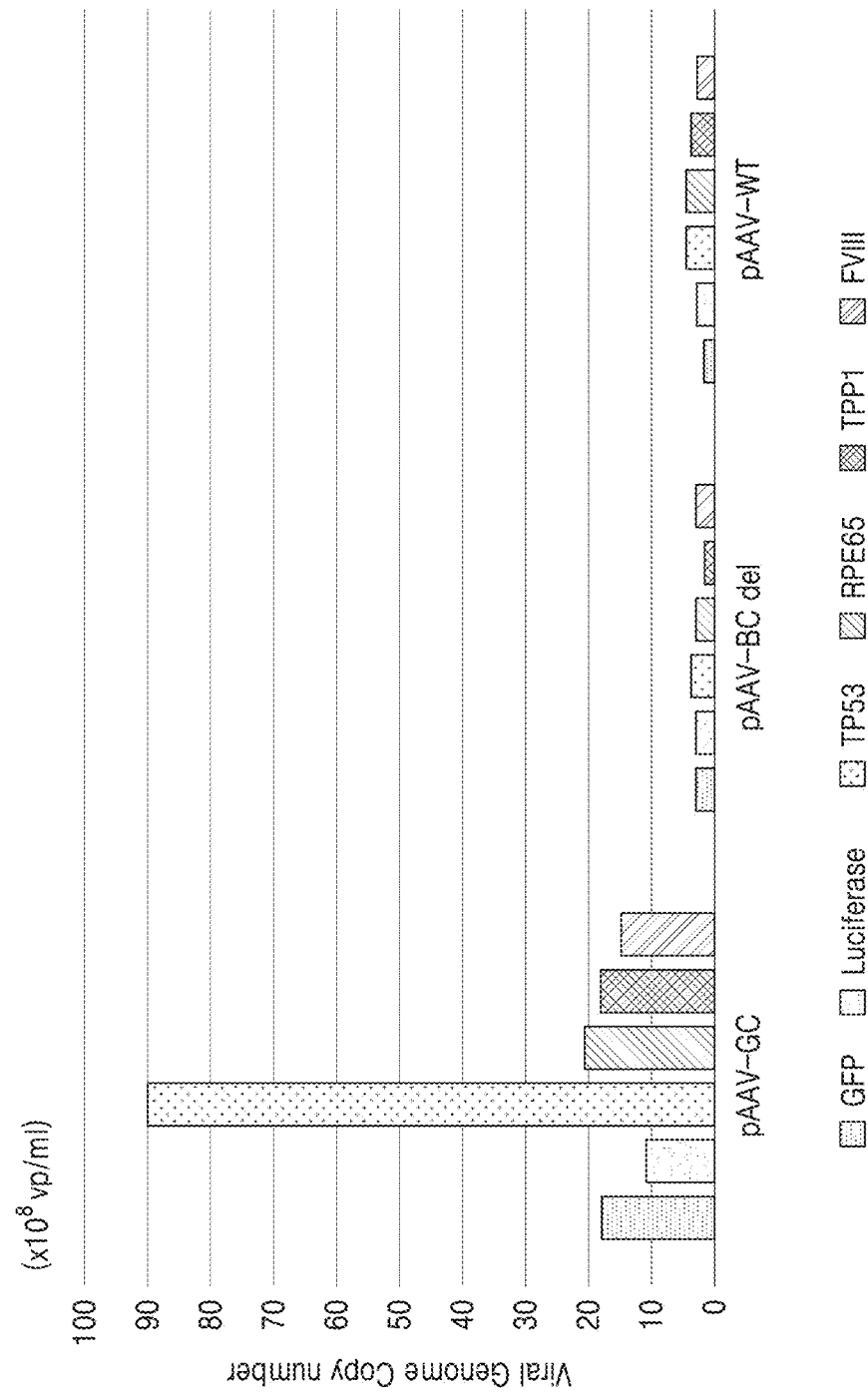
FIG. 6 is results of qPCR virus genome quantification confirming productivity of AAVs of the pAAV-GC vector, the pAAV-WT vector, and the pAAV-BC del vector for expressing various genes (GFP, Luciferase, TP53, RPE65, TPP1, or FVIII).

FIG. 6 is results of qPCR virus genome quantification confirming productivity of AAV of the pAAV-GC vector, the pAAV-WT vector, and the pAAV-BC del vector for expressing various genes (GFP, Luciferase, TP53, RPE65, TPP1, or FVIII).

As a result, as shown in FIGS. 4 to 6, it was confirmed that the pAAV-GC vector had remarkably high AAV productivity even when various genes were introduced, compared to the pAAV-WT vector and the pAAV-BC del vector.

Therefore, it was found that since the pAAV-GC vector including the asymmetrically modified ITR partially omits a self-replication process in the host cell, packaging efficiency into viral particles is increased within the same production period, and therefore, productivity of the pAAV-GC vector was improved compared to the existing AAV delivery vehicles, due to increased self-replication efficiency.

Experimental Example 2. Confirmation of Rate of Gene Expression of AAV Complex 2-1. Confirmation of Rate of Expression of GFP Gene A rate of expression of a target gene of a recombinant AAV complex according to an embodiment was confirmed. Specifically, HEK293, a normal fetal kidney-derived cell line, was respectively infected with the same amount of AAV complexes (Example 1, Comparative Example 1, or Comparative Example 2). After 72 hours, GFP signals expressed by the cells were photographed by using an inverted fluorescence microscope. Then, each cell was disrupted to purify the proteins, the samples were loaded on an SDS page gel, and rates of expression of the GFP gene were confirmed through Western blotting. Western blot band intensities were quantified by using image J software. The degree of GFP protein detection in the sample treated with pAAV-GC vectors having the strongest band intensity was set as 100%, and each rate of gene expression was quantified as a relative value. Two biological replicates were used for each group.

Figure 7:
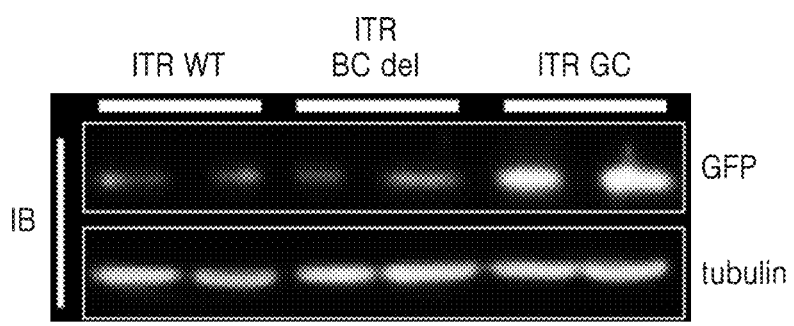
FIG. 7 is results of confirming expression of a transgene GFP in AAV complexes according to ITR types (ITR WT, ITR BC del, or ITR GC), by Western blot.

FIG. 7 is results of confirming expression of a transgene GFP in AAV complexes according to ITR types (ITR WT, ITR BC del, or ITR GC), by Western blot.

Table 3 shows results of quantifying relative expression rates (%) of the transgene GFP in AAV complexes according to the ITR types.

TABLE 3

| ITR type | Relative expression rate (%) |
| --- | --- |
| pAAV-WT (Comparative Example 1) | 29.52 |
| pAAV-WT (Comparative Example 1) | 30.02 |
| pAAV-BC del (Comparative Example 2) | 35.85 |
| pAAV-BC del (Comparative Example 2) | 43.63 |
| pAAV-GC (Example 1) | 97.68 |
| pAAV-GC (Example 1) | 100 |

As a result, as shown in FIG. 7 and Table 3, it was confirmed that the rate of expression of the GFP gene was remarkably high when the pAAV-GC vector (Example 1) was used, compared to when the pAAV-WT vector (Comparative Example 1) and the pAAV-BC del vector (Comparative Example 2) were used.

2-2. Confirmation of Rates of Expression of Various Gene

Experiments were performed to confirm rates of expression of various transgenes GFP, luciferase, TP53, RPE65, TPP1, and FVIII by using Examples 1 to 6 and Comparative Examples 1 to 12 in the same manner as in Experimental Example 2-1.

For GFP and luciferase genes, the same cell line as used in Experimental Example 2-1 was used. For TP53, TPP1, RPE65, and FVIII genes, HEK293 cells in which each gene was knocked out by using CRISPR/Cas9 (Synthego, USA) were used to eliminate effects of endogenous genes uniquely present in target cells.

After confirming that expression of endogenous genes did not occur in the cell line, the cells were cultured in a 6-well cell culture plate. A concentration of a viral solution was adjusted so that $1.0 \times 10^8$ virus particles were treated per $1.0 \times 10^5$ cells, and the viral solution was treated to the cells. Two days after AAV treatment, proteins expressed from each introduced gene were detected by the Western blot (WB) method. In this regard, antibodies used were as follows: GFP (Invitrogen A-11122), luciferase (Invitrogen PA1-179), TP53 (MA5-14067), TPP1 (PA5-102819), RPE65 (MA1-16578), and FVIII (PA5-104451). WB band intensities were quantified by using image J software. The resulting band of pAAV-GC was regarded as 100%, and bands of pAAV-WT and pAAV-BC del were quantified as relative values. Three biological replicates were used for each group.

Table 4 is results of quantifying relative expression rates (%) of a transgene in AAV complexes according to ITR types (pAAV-GC, pAAV-BC del, or pAAV-WT).

Figure 8:
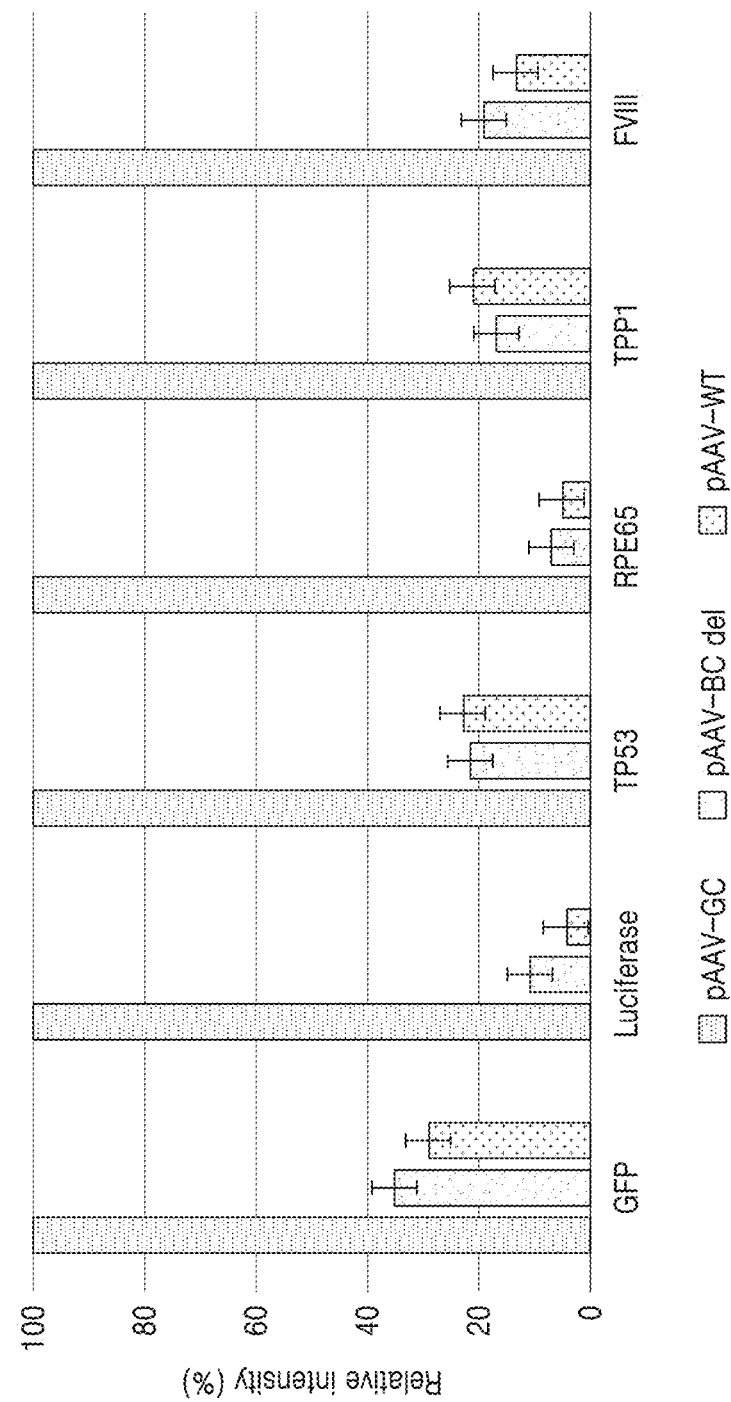
FIG. 8 shows relative expression rates (%) of a transgene in AAV complexes according to ITR types (pAAV-GC, pAAV-BC del, or pAAV-WT).

FIG. 8 shows relative expression rates (%) of a transgene in AAV complexes according to ITR types (pAAV-GC, pAAV-BC del, or pAAV-WT).

TABLE 4

|  | GFP | Luciferase | TP53 | RPE65 | TPP1 | FVIII |
| --- | --- | --- | --- | --- | --- | --- |
| pAAV-GC | 100 | 100 | 100 | 100 | 100 | 100 |
| pAAV-GC | 97.7 | 98.2 | 97.5 | 98.4 | 99.8 | 98.5 |
| pAAV-GC | 99.4 | 92.4 | 96.5 | 98.6 | 97.1 | 95.8 |
| pAAV-BC del | 35.9 | 11.4 | 22.3 | 7.8 | 17.4 | 19.5 |
| pAAV-BC del | 37.8 | 14.5 | 19.5 | 8.8 | 16.6 | 17.4 |
| pAAV-BC del | 43.6 | 12.7 | 18.9 | 7.9 | 18.9 | 17.1 |
| pAAV-WT | 29.5 | 4.8 | 23.4 | 5.7 | 21.5 | 13.8 |
| pAAV-WT | 30.1 | 4.5 | 11.8 | 6.8 | 19.8 | 11.1 |
| pAAV-WT | 28.9 | 7.4 | 19.4 | 4.9 | 23.5 | 16.4 |

As a result, as shown in Table 4 and FIG. 8, rates of expression of all transgenes were about 2-fold to about 10-fold higher, when the pAAV-GC vector including the asymmetrically modified ITR was used, compared to when the pAAV-WT vector including the unmodified symmetric ITR and the symmetrically modified pAAV-BC del vector were used.

Accordingly, it was found that the pAAV-GC vector including the asymmetrically modified ITR may be used as a delivery vehicle platform with significantly increased transgene expression efficiency to deliver various transgenes into target cells.

Experimental Example 3. Confirmation of Genotoxicity of AAV Complex 3-1. Confirmation of Insertion of Transgene GFP into Host Chromosome An experiment was performed to confirm that a transgene is not recombined with a target cell chromosome when the recombinant AAV complex according to an embodiment is used.

Specifically, H460 cells were infected with pAAV-GC (Example 1), pAAV-WT (Comparative Example 1), and pAAV-BC del (Comparative Example 2) loaded with a GFP gene, respectively. Cells expressing GFP were isolated and the same number of cells were inoculated into a culture dish. The cells were subcultured by diluting by a ratio of ⅓ every 3 days, and whether the GFP gene was genetically transmitted to the next generation was confirmed by tracking rates of expression of the GFP gene.

FIG. 9A shows results of taking images of GFP expression by using a fluorescence microscope at passage numbers P3 and P10.

Table 5 is results of confirming ratios of GFP-expressing cells in cultures of subculture passage numbers of P1 to P10.

TABLE 5

|  | P1 | P2 | P3 | P4 | P5 | P6 | P7 | P8 | P9 | P10 |
|---|---|---|---|---|---|---|---|---|---|---|
| pAAV-GC (Example 1) | 99.000% | 32.870% | 11.230% | 3.760% | 1.040% | 0.230% | 0.014% | 0.005% | 0.002% | 0.001% |
| pAAV-BC del. (Comparative Example 2) | 99.000% | 33.020% | 10.990% | 3.880% | 1.100% | 0.180% | 0.190% | 0.250% | 0.350% | 0.530% |
| pAAV-WT ITR (Comparative Example 1) | 99.000% | 32.960% | 11.340% | 3.650% | 1.080% | 0.220% | 0.210% | 0.310% | 0.410% | 0.580% |

Figure 9B:
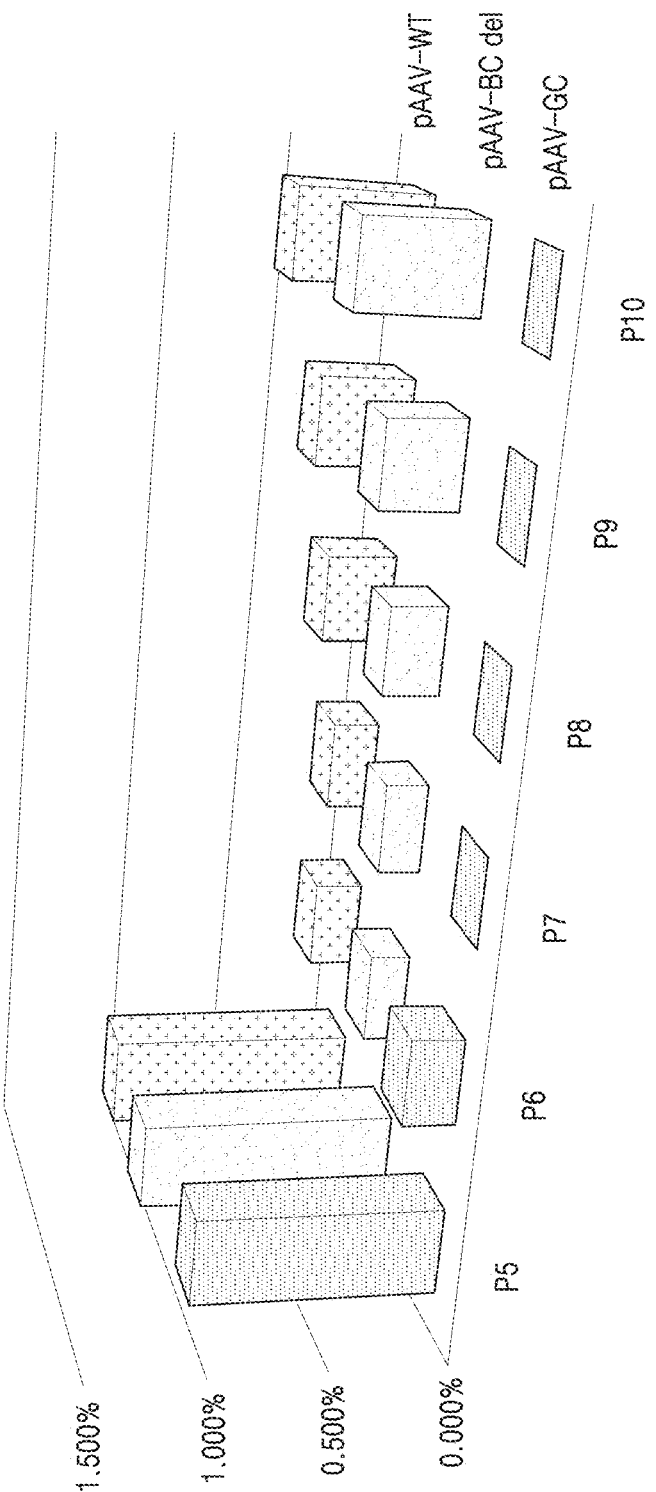
FIG. 9B shows results of schematizing Table 4 in which ratios of GFP-expressing cells are quantified.

FIG. 9B is results of schematizing Table 4 in which ratios of GFP-expressing cells are quantified.

As a result, as shown in FIGS. 9A and 9B and Table 5, expression of GFP, a transgene, was very rarely observed in cells infected with the pAAV-GC vector (Example 1) after P7. On the other hand, it was confirmed that GFP, a transgene, was continuously observed in cells infected with the pAAV-WT vector (Comparative Example 1) or the pAAV-BC del vector (Comparative Example 2).

Accordingly, it was confirmed that genotoxicity of genes transferred to the next generation was significantly reduced in the AAV complex of Example 1 compared to the AAV complexes of Comparative Examples 1 and 2.

3-2. Confirmation of Insertion of Various Transgenes into Host Chromosome

Experiments were performed to confirm insertion of various transgenes GFP, luciferase, TP53, RPE65, TPP1, and FVIII into a host chromosome by using Examples 1 to 6 and Comparative Examples 1 to 12 in the same manner as in Experimental Example 3-1.

For GFP and luciferase genes, the same cell line as used in Experimental Example 3-1 was used. For TP53, TPP1, RPE65, and FVIII genes, HEK293 cells in which each gene was knocked out by using CRISPR/Cas9 (Synthego, USA) were used to eliminate effects of endogenous genes uniquely present in the target cells.

After confirming that endogenous gene expression did not occur in the cell line, proteins expressed from each gene introduced by AAV were detected by Western blotting. In this regard, antibodies used were as follows: GFP (Invitrogen A-11122), luciferase (invitrogen PA1-179), TP53 (MA5-14067), TPP1 (PA5-102819), RPE65 (MA1-16578), and FVIII (PA5-104451). WB band intensities were quantified by using image J software. The resulting band of pAAV-WT was regarded as 100%, and bands of pAAV-GC and pAAV-BC del were quantified as relative values.

Table 6 shows results (%) of relative gene expression levels at a subculture passage number P7.

TABLE 6

|  | GFP | Luciferase | TP53 | RPE65 | TPP1 | FVIII |
|---|---|---|---|---|---|---|
| pAAV-GC | 1.4 | 0 | 7.4 | 5.1 | 2.2 | 2.4 |
| pAAV-BC del | 94.7 | 88.2 | 92.4 | 74.1 | 81.7 | 95.4 |
| pAAV-WT | 100 | 100 | 100 | 100 | 100 | 100 |

Figure 10:
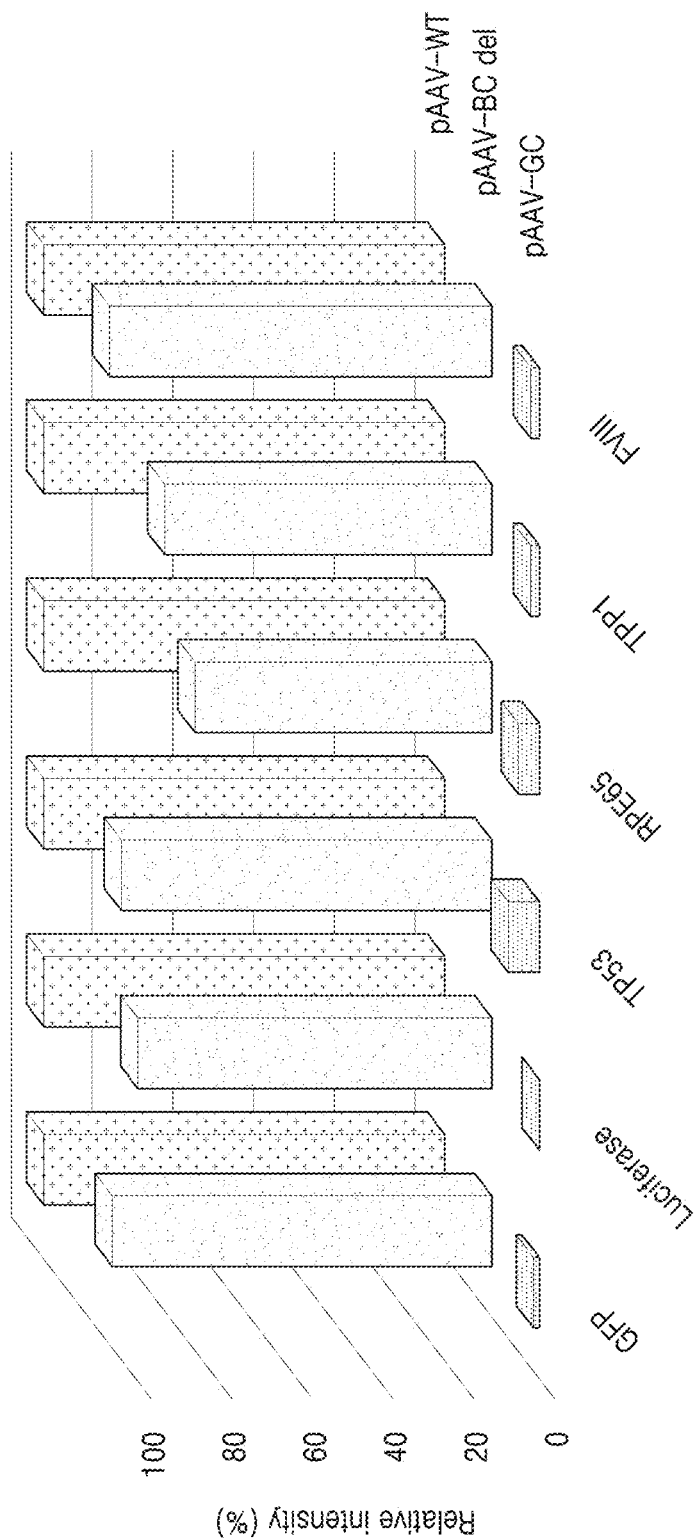
FIG. 10 shows results of schematizing Table 5 in which relative gene expression levels at P7 are quantified.

FIG. 10 is results of schematizing Table 5 quantifying relative gene expression levels at P7.

As a result, as shown in Table 6 and FIG. 10, expression of the transgene was very rarely observed in cells infected with the pAAV-GC vector at P7. On the other hand, it was confirmed that expression of the transgene was continuously observed in the cells infected with the pAAV-WT vector or the pAAV-BC del vector.

Therefore, it was confirmed that the pAAV-GC vector including an asymmetrically modified ITR had significantly reduced genotoxicity of transferring a transgene to the next generation compared to the pAAV-WT vector including an unmodified symmetrical ITR and the symmetrically modified pAAV-BC del vector.

3-3. Determining Whether Transgene Forms Concatemer in Target Cells

An experiment was performed to determine whether or not a concatemer, which is found when a transgene is inserted into a host chromosome, is formed, when the transgene was delivered to the host cell by using an AAV vector.

Specifically, at P7 of Experimental Example 3-1, DNA was extracted from each of the GFP expressing cells. The extracted DNA was amplified by PCR and subjected to electrophoresis to identify a remaining form of the DNA transferred to the host cell.

Figure 11:
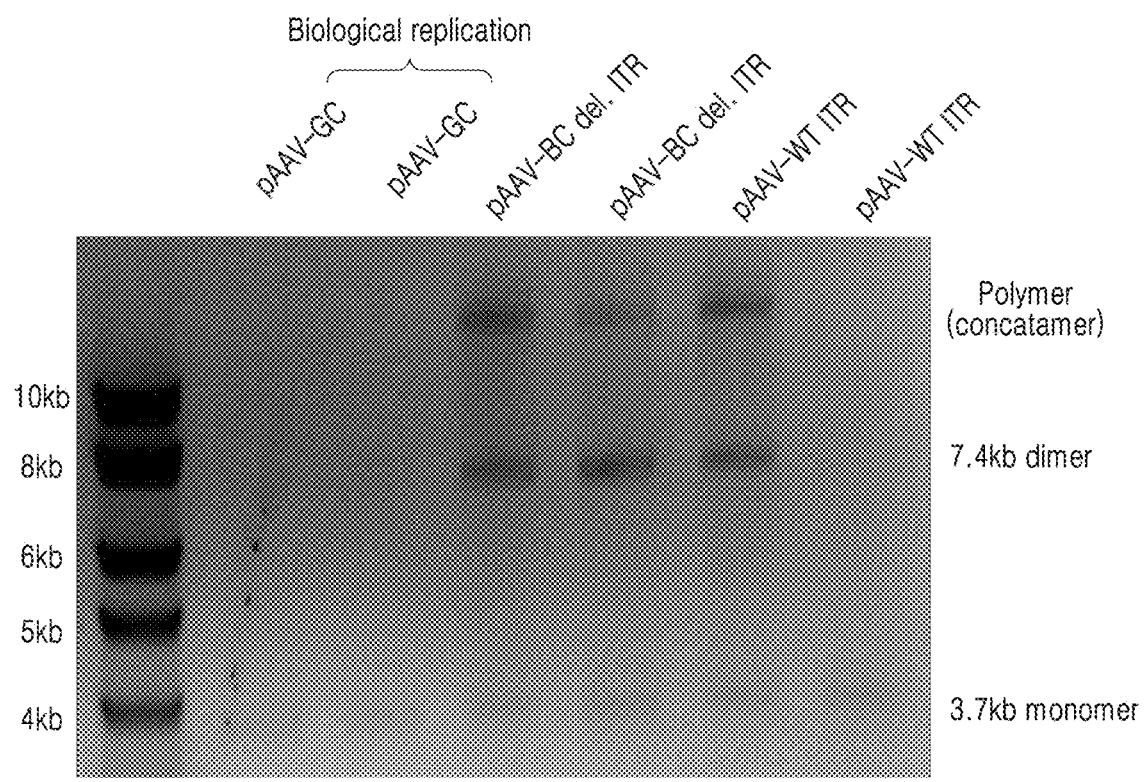
FIG. 11 shows results of PCR amplification confirming the presence or absence of concatemer formation of a transgene in a host cell.

FIG. 11 is results of PCR amplification confirming the presence or absence of concatemer formation of a transgene in the host cell.

As a result, as shown in FIG. 11, it was confirmed that the pAAV-GC vector (Example 1) in which one hairpin structure was missing in one ITR, could not form a concatemer, which is a well-known characteristic of AAV vectors. On the other hand, in cases of the pAAV-WT vector (Comparative Example 1) and the pAAV-BC del vector (Comparative Example 2), in which both ITRs have a hairpin structure, the transgenes were observed in various forms of polymers such as monomers, dimers, or concatemers.

Accordingly, it was confirmed that when the pAAV-GC vectors were used, the transgenes did not form a concatemer structure in the host cell and thus, an integration into the chromosome of the host cell was suppressed.

All in all, it was seen that the pAAV-GC vector including an asymmetrically modified ITR is suitable as a delivery vehicle for high-efficiency expression of a transgene in a short period of time while suppressing long-term expression of the transgene in the host cell.

The above description of the present disclosure is for illustrative purposes, and those skilled in the art to which the present disclosure belongs will be able to understand that the examples and embodiments can be easily modified without changing the technical idea or essential features of the disclosure. Therefore, it should be understood that the above examples are not limitative, but illustrative in all aspects.

An AAV complex according to an aspect has advantages of increased productivity and expression efficiency of a transgene, and decreased genotoxicity, by having an asymmetric ITR in which any one of two ITRs is modified, and therefore, may be used as an AAV delivery vehicle platform.

Specifically, an AAV complex according to an aspect has the following advantages:

1. The AAV complex partially omits a self-replication process in a host cell (or a packaging cell) due to a deletion of any one ITR among two ITRs, and thus, packaging efficiency into viral particles is increased within the same production period, and therefore, self-replication efficiency is increased, and productivity of the AAV complex is improved compared to existing AAV complexes.

2. A rate of expression (amount of expression) of a transgene is higher than that of a general wild-type (WT) AAV.

3. A genome of WT AAV forms a concatemer structure that is essential for recombination of transgenes within infected cells. That is, it has been reported that a transgene is inserted into a chromosome of a host cell by forming a concatemer structure in a form of a polymorph in which several identical genomes are linked. On the other hand, since the AAV complex according to an aspect has an asymmetrically modified ITR, it does not form a concatemer structure and thus suppresses insertion (that is, recombination) of the transgene into the host chromosome. Thus, there is an advantage of reduced genotoxicity.

4. An AAV complex having an asymmetrically modified ITR according to an aspect is an AAV delivery vehicle platform in which productivity and a rate of expression of the transgene is enhanced and genotoxicity is reduced, and thus, various genes may be delivered into target cells by using the platform.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. An adeno-associated virus (AAV) complex, comprising a polynucleotide sequence encoding a transgene between a first inverted terminal repeat (ITR) and a second ITR, wherein the first ITR is not modified and the second ITR is modified, wherein in the second ITR, all or part of a stem-loop structure, which is formed of rep-binding element (RBE), RBE', A, A', B, B', C, C', and D regions, is modified, wherein the modified ITR exists as an open-end without forming any of the stem region and the loop region of the stem-loop structure.

2. The adeno-associated virus complex of claim 1, further comprising an operably linked promoter, a polynucleotide sequence encoding a transgene, and a polyadenylation sequence, between the first ITR and the second ITR.

3. The adeno-associated virus complex of claim 1, wherein the AAV is of an AAV serotype selected from the group consisting of AAV1, AAV2, AAV3, AAV4, AAV5, AAV6, AAV7, AAV8, AAV9, AAV10, AAV11, and AAV12.

4. The adeno-associated virus complex of claim 1, wherein in the second ITR, all of B, B', C, C', and RBE' regions are deleted, and either A or A' region, whichever is closer to 3'-end of (+) strand of the transgene or 5'-end of (−) strand of the transgene, is deleted.

5. The adeno-associated virus complex of claim 1, wherein the second ITR comprises a terminal resolution site (trs) sequence and an RBE sequence.

6. The adeno-associated virus complex of claim 2, wherein the promoter is a tissue-specific promoter.

7. The adeno-associated virus complex of claim 1, wherein the transgene is a therapeutic gene.

8. The adeno-associated virus complex of claim 1, wherein the transgene is GFP, Luciferase, TP53, RPE65, TPP1, or FVIII.

9. A composition comprising the adeno-associated virus complex of claim 1 and a pharmaceutically acceptable carrier.

* * * * *

(12) EX PARTE REEXAMINATION CERTIFICATE (257th)
Ex Parte Reexamination Ordered under 35 U.S.C. 257

United States Patent
Bae et al.

(10) Number: US 11,891,617 C1
(45) Certificate Issued: Aug. 12, 2025

(54) MODIFIED COMPLEX PLATFORM OF ADENO-ASSOCIATED VIRUS WITH IMPROVED RATE OF EXPRESSION OF LOADED GENES AND REDUCED GENOTOXICITY

(71) Applicant: GENECRAFT INC., Cheongju-si (KR)

(72) Inventors: Suk Chul Bae, Cheongju-si (KR); You Soub Lee, Cheongju-si (KR); Xinzi Chi, Cheongju-si (KR); Tae Geun Park, Cheongju-si (KR); Woo-Jin Kim, Seoul (KR)

(73) Assignee: GENECRAFT INC., Cheongju-si (KR)

Supplemental Examination Request:
No. 96/050,033, Mar. 22, 2024

Reexamination Certificate for:
Patent No.: 11,891,617
Issued: Feb. 6, 2024
Appl. No.: 18/190,630
Filed: Mar. 27, 2023

(51) Int. Cl.
*C12N 15/86* (2006.01)

(52) U.S. Cl.
CPC .... *C12N 15/86* (2013.01); *C12N 2750/14143* (2013.01); *C12N 2750/14145* (2013.01)

(58) Field of Classification Search
None
See application file for complete search history.

(56) References Cited

To view the complete listing of prior art documents cited during the supplemental examination proceeding and the resulting reexamination proceeding for Control Number 96/050,033, please refer to the USPTO's Patent Electronic System.

*Primary Examiner* — Padmashri Ponnaluri

(57) ABSTRACT

Described herein is an adeno-associated virus (AAV) complex platform including an asymmetrically modified inverted terminal repeat (ITR). The AAV complex has advantages of increased productivity and expression efficiency of a transgene, and decreased genotoxicity, by having an asymmetric ITR in which any one of two ITRs is modified. Also, described herein is a composition comprising the adeno-associated virus complex and a method of gene therapy.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 4 are determined to be patentable as amended.

Claims 3 and 6-9, dependent on an amended claim, are determined to be patentable.

Claims 2 and 5 were not reexamined.

1. An adeno-associated virus (AAV) complex, comprising a polynucleotide sequence encoding a transgene between a first inverted terminal repeat (ITR) and a second ITR, wherein the first ITR is not modified and the second ITR is modified, wherein in the second ITR, all or part of a stem-loop structure, which is formed of *rep*-binding element (RBE), RBE', A, A', B, B', C, C', and D regions, is modified, wherein the modified *second* ITR exists as an open-end[without forming any of],

*wherein the modified second ITR does not form* the stem region and the loop region of the stem-loop structure, *and*

*wherein the modified second ITR does not form a hairpin structure.*

4. The adeno-associated virus complex of claim 1, wherein in the *modified* second ITR, all of B, B', C, C', and RBE' regions are deleted, and either A or A' region, whichever is closer to 3'-end of (+) strand of the transgene or 5'-end of (−) strand of the transgene, is deleted, *wherein the modified second ITR exists as an open-end.*

* * * * *